United States Patent
Lim et al.

(10) Patent No.: US 10,449,331 B2
(45) Date of Patent: Oct. 22, 2019

(54) CATHETER DEVICES WITH SEALS AND RELATED METHODS

(71) Applicant: B. BRAUN MELSUNGEN AG, Melsungen (DE)

(72) Inventors: Wen Jenn Lim, Penang (MY); Hui Kuun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 746 days.

(21) Appl. No.: 14/711,704

(22) Filed: May 13, 2015

(65) Prior Publication Data

US 2016/0331936 A1   Nov. 17, 2016

(51) Int. Cl.
| | | |
|---|---|---|
| A61M 25/06 | (2006.01) | |
| A61M 25/00 | (2006.01) | |
| A61M 5/158 | (2006.01) | |
| A61M 39/06 | (2006.01) | |

(52) U.S. Cl.
CPC ........ *A61M 25/0606* (2013.01); *A61M 5/158* (2013.01); *A61M 25/0014* (2013.01); *A61M 25/0075* (2013.01); *A61M 25/0097* (2013.01); *A61M 39/0693* (2013.01); *A61M 25/0618* (2013.01); *A61M 25/0693* (2013.01); *A61M 2039/062* (2013.01); *A61M 2039/064* (2013.01); *A61M 2039/066* (2013.01); *A61M 2039/0653* (2013.01)

(58) Field of Classification Search
CPC .......................... A61M 25/06; A61M 25/0606
See application file for complete search history.

(56) References Cited

U.S. PATENT DOCUMENTS

| | | | | |
|---|---|---|---|---|
| 3,324,854 A | * | 6/1967 | Weese | A61M 5/425 604/115 |
| 5,053,014 A | * | 10/1991 | Van Heugten | A61M 39/26 604/167.03 |
| 5,171,214 A | * | 12/1992 | Kolber | A61J 1/2096 206/222 |
| 5,334,159 A | * | 8/1994 | Turkel | A61B 17/3496 604/158 |

(Continued)

FOREIGN PATENT DOCUMENTS

| | | |
|---|---|---|
| CN | 203694357 | 7/2014 |
| WO | WO 2007/050788 | 5/2007 |

OTHER PUBLICATIONS

International Search Report and Written Opinion on corresponding PCT application (PCT/EP2016/060519) from International Searching Authority (EPO) dated Aug. 10, 2016.

(Continued)

*Primary Examiner* — Bhisma Mehta
*Assistant Examiner* — Matthew A Engel
(74) *Attorney, Agent, or Firm* — Klein, O'Neill & Singh, LLP

(57) ABSTRACT

Needle devices are described. The needle devices can have a catheter hub, a needle hub, and a valve system for controlling fluid flow through the catheter hub. The valve system can include a valve and a valve retainer. The valve can have flow holes for fluid flow therethrough or can have a valve piece for controlling flow through flow holes located externally of the valve. A needle guard is usable with the needle device to block a tip of the needle. A valve opener can also be used to open the valve.

41 Claims, 10 Drawing Sheets

(56) References Cited

U.S. PATENT DOCUMENTS

| | | | | |
|---|---|---|---|---|
| 5,393,497 A * | 2/1995 | Haber | A61J 1/2089 | 137/68.11 |
| 6,569,123 B2 * | 5/2003 | Alchas | A61M 5/32 | 604/192 |
| 6,616,630 B1 * | 9/2003 | Woehr | A61M 5/3273 | 604/110 |
| 7,217,258 B2 * | 5/2007 | Caizza | A61M 5/3216 | 604/240 |
| 8,647,313 B2 * | 2/2014 | Woehr | A61M 5/158 | 604/158 |
| 2001/0053895 A1 * | 12/2001 | Vaillancourt | A61M 25/0606 | 604/243 |
| 2002/0168530 A1 * | 11/2002 | Tingey | A61L 29/085 | 428/421 |
| 2010/0137831 A1 * | 6/2010 | Tsals | A61M 5/3243 | 604/506 |
| 2010/0204648 A1 * | 8/2010 | Stout | A61M 25/0606 | 604/122 |
| 2010/0204660 A1 * | 8/2010 | McKinnon | A61M 25/0606 | 604/244 |
| 2010/0204675 A1 * | 8/2010 | Woehr | A61B 5/1411 | 604/500 |
| 2011/0160662 A1 * | 6/2011 | Stout | A61M 25/0097 | 604/122 |
| 2011/0160663 A1 * | 6/2011 | Stout | A61M 25/0009 | 604/122 |
| 2013/0090607 A1 * | 4/2013 | McKinnon | A61M 25/0097 | 604/247 |
| 2014/0276434 A1 * | 9/2014 | Woehr | A61M 25/0075 | 604/164.08 |

OTHER PUBLICATIONS

International Preliminary Report on Patentability on corresponding PCT application (PCT/EP2016/060519) from International Searching Authority (EPO) dated Nov. 23, 2017.

* cited by examiner

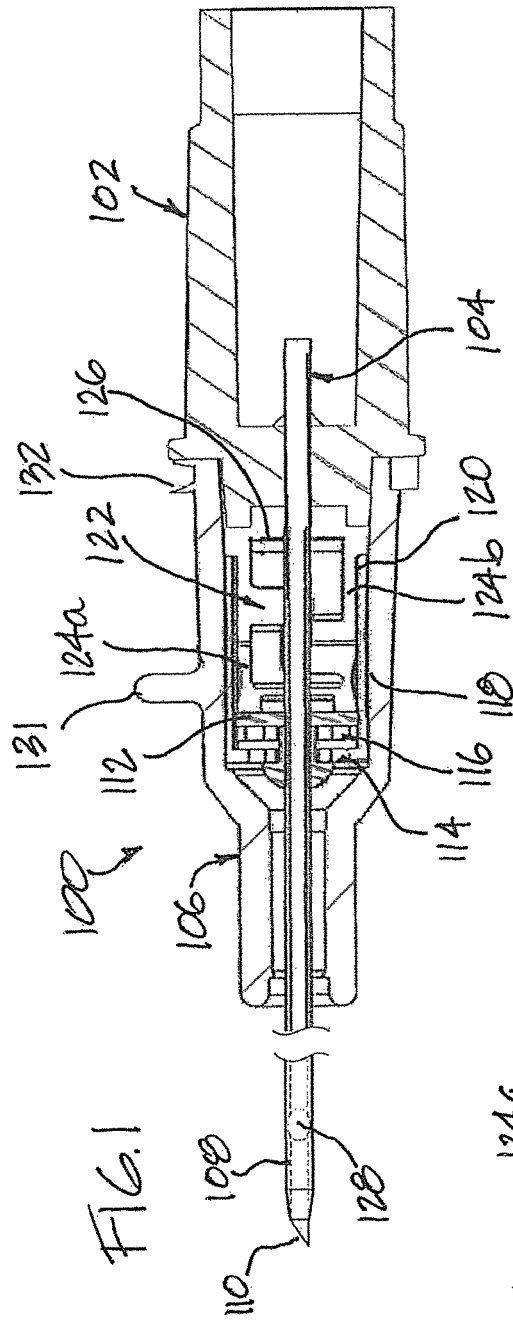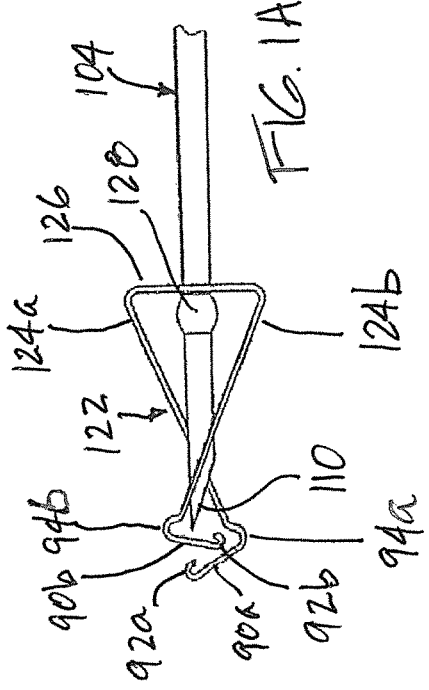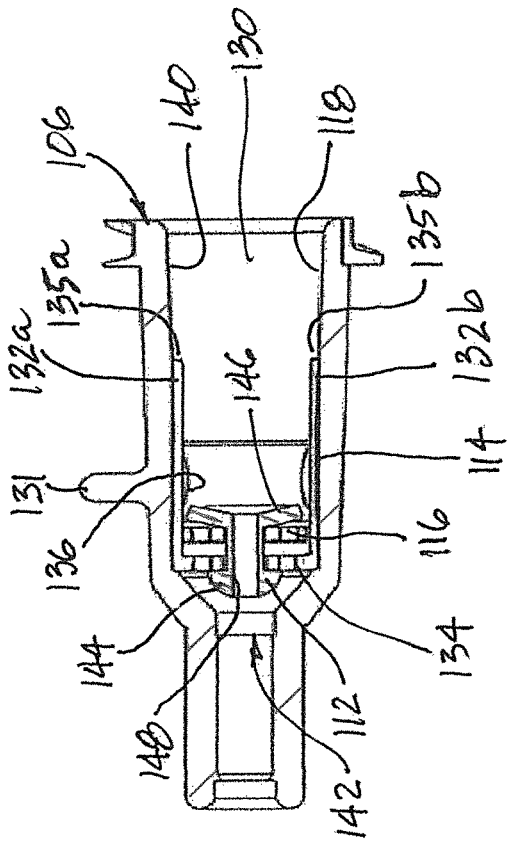

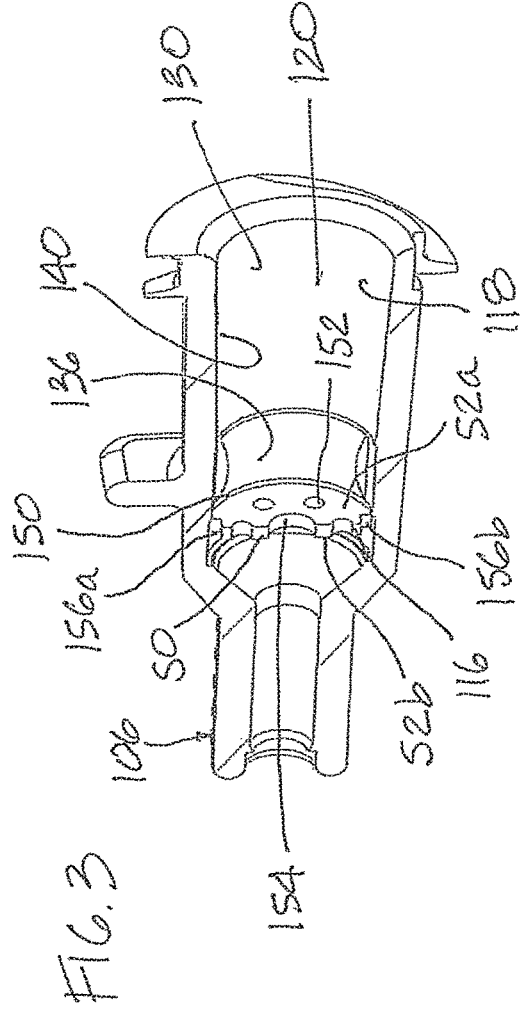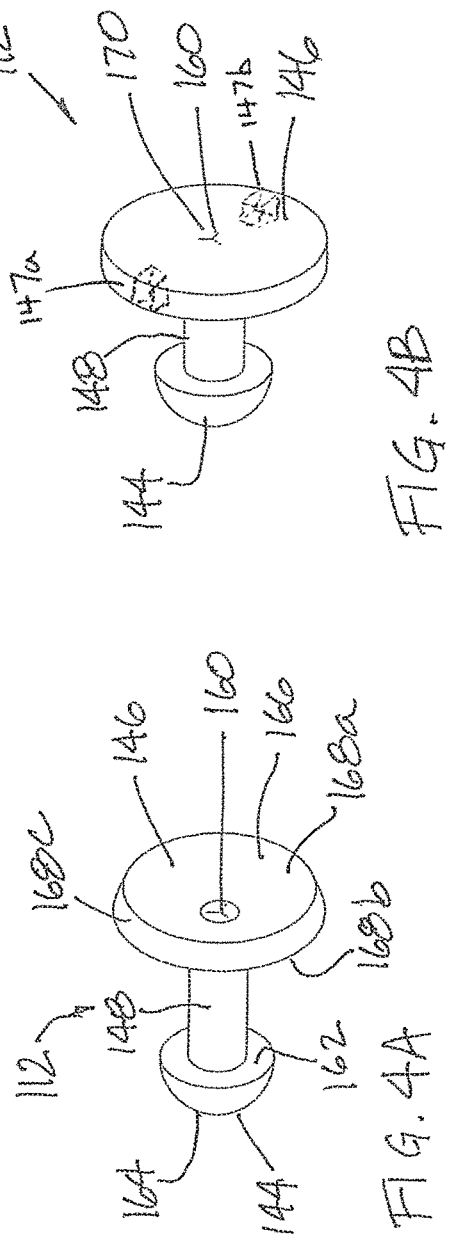

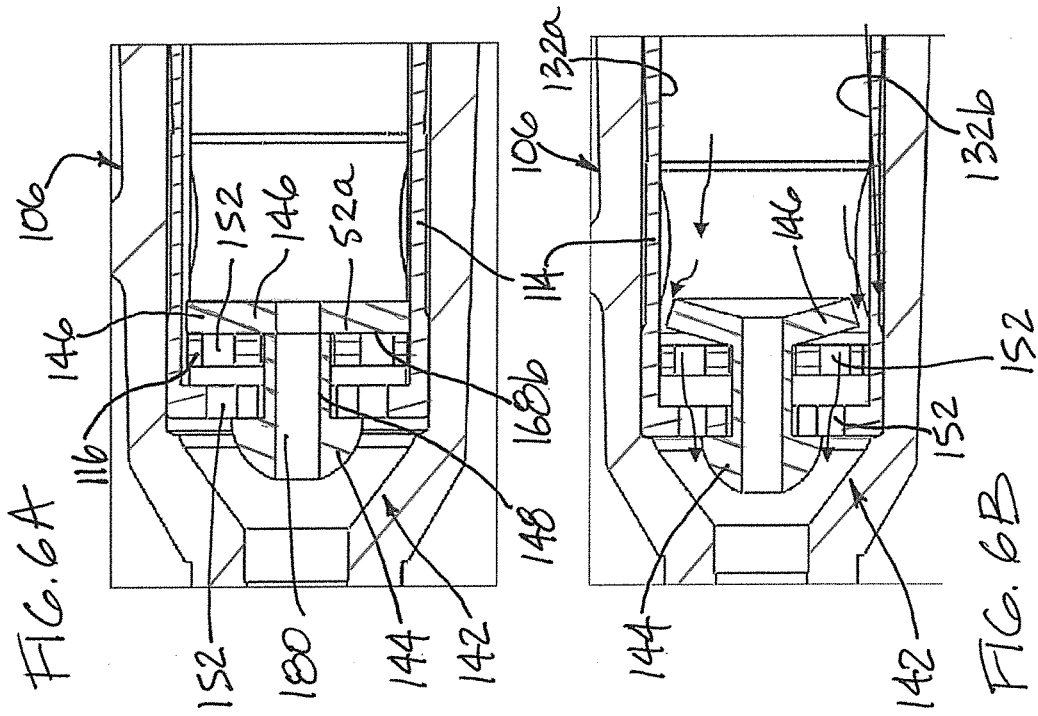
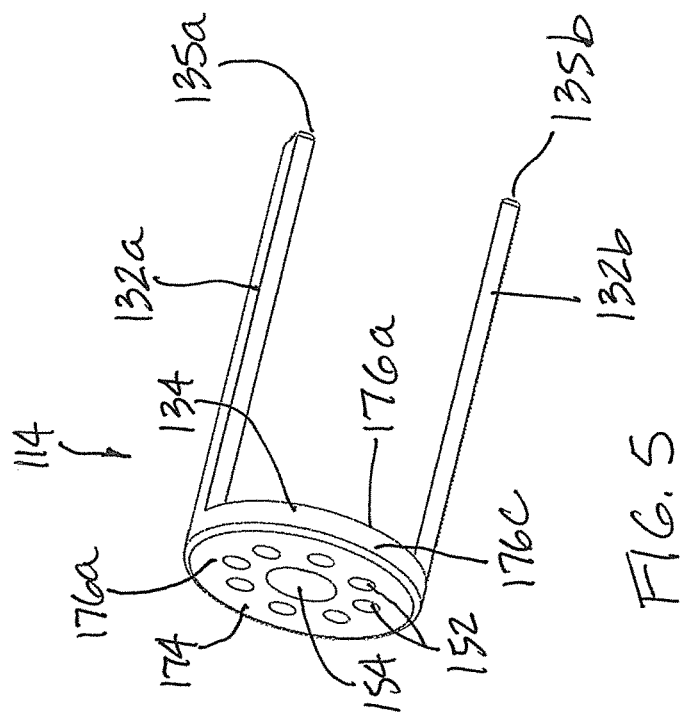

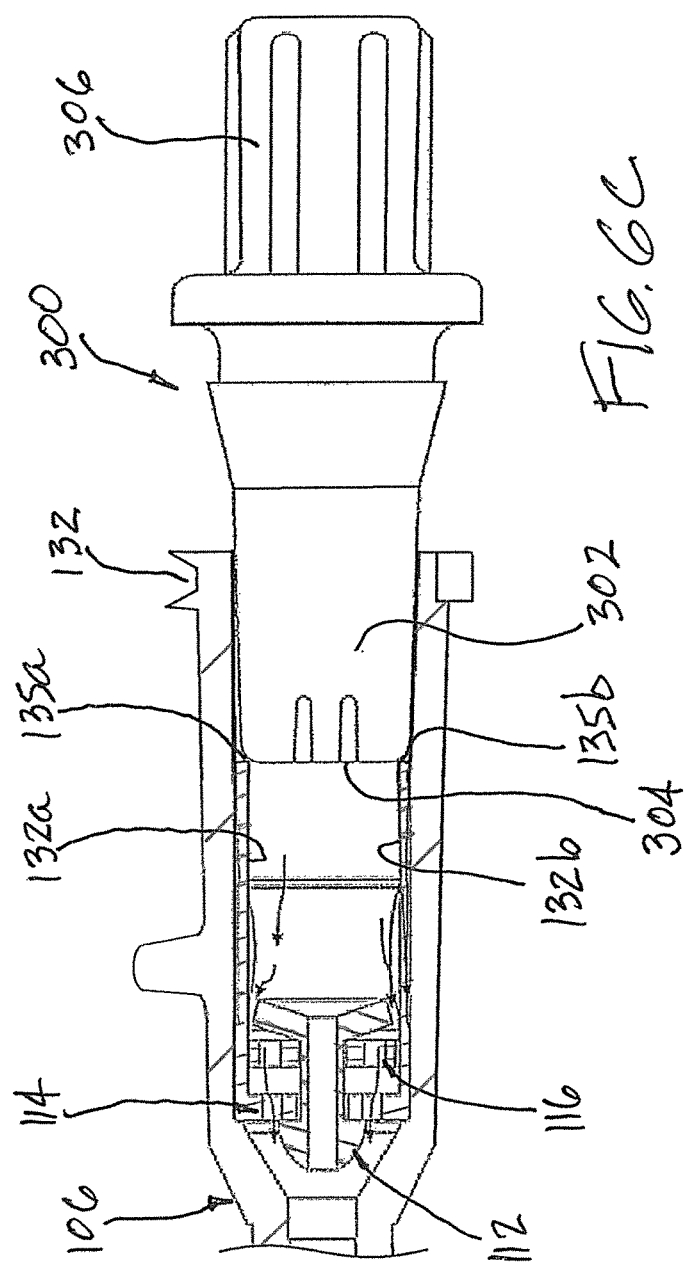

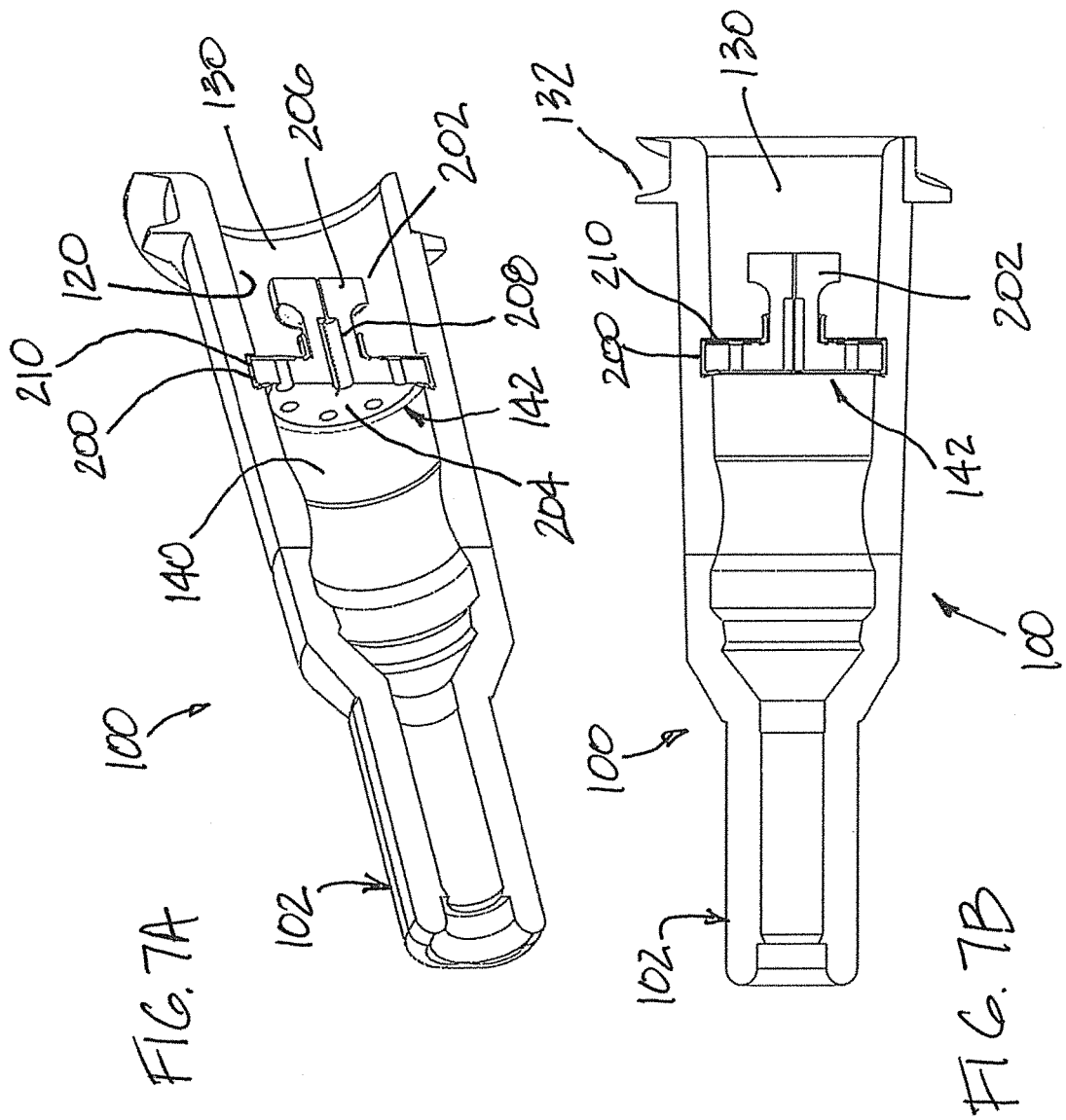

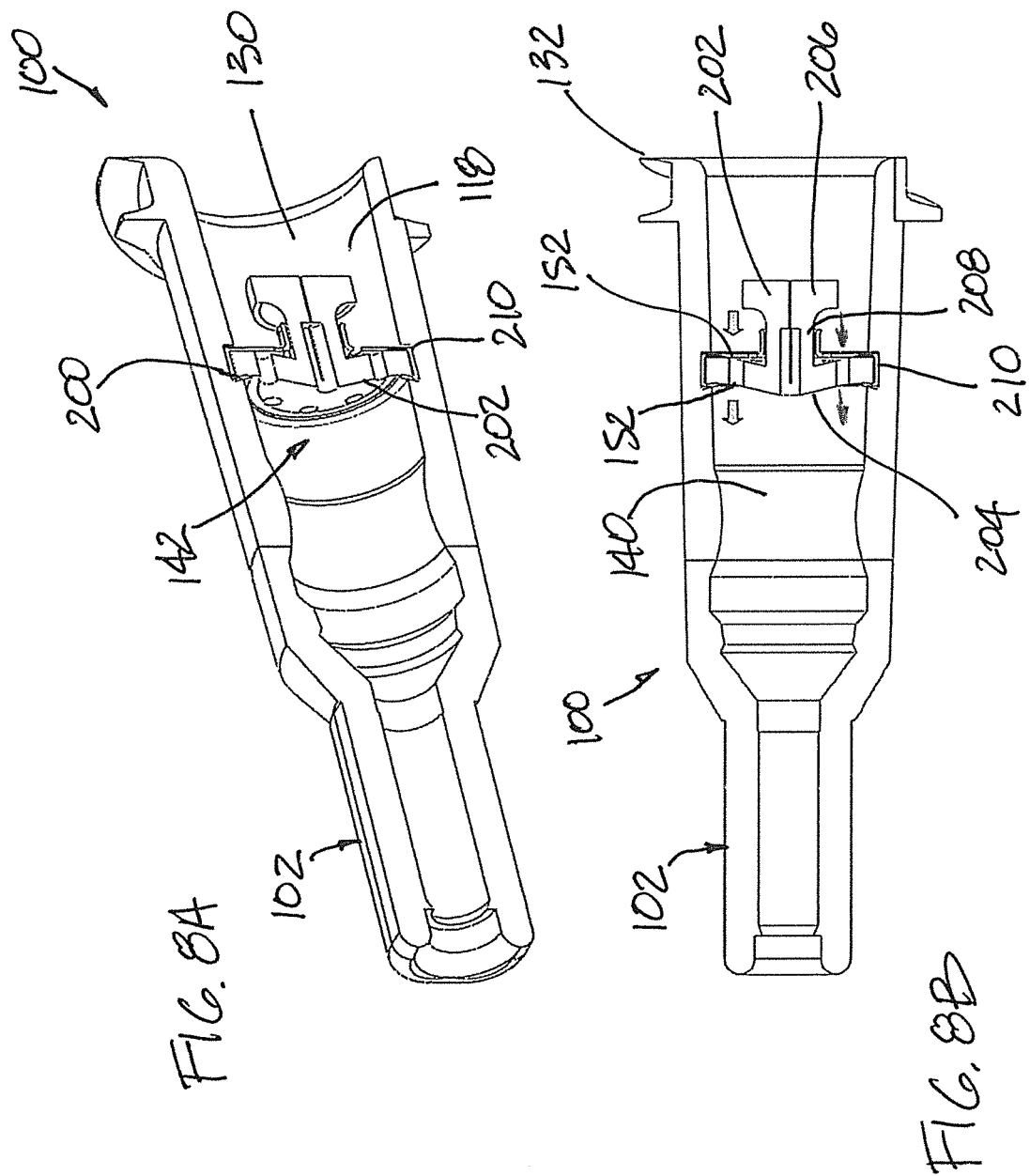

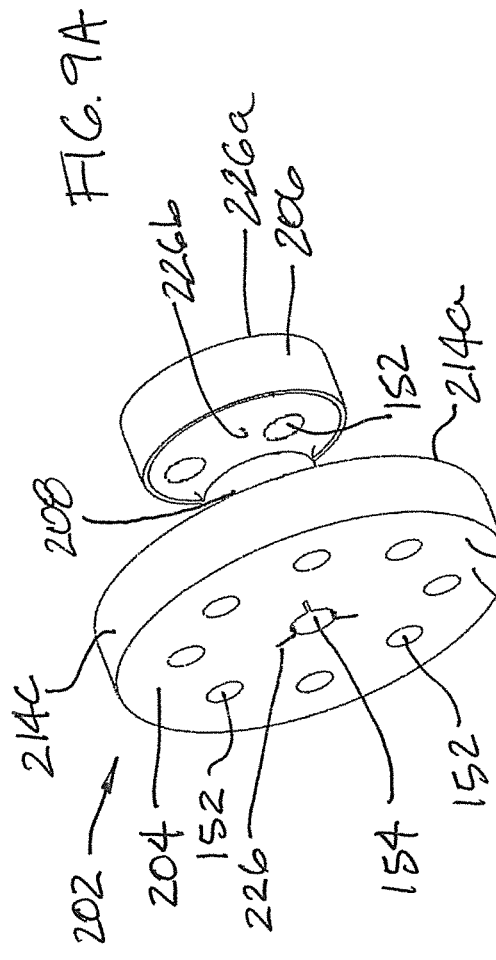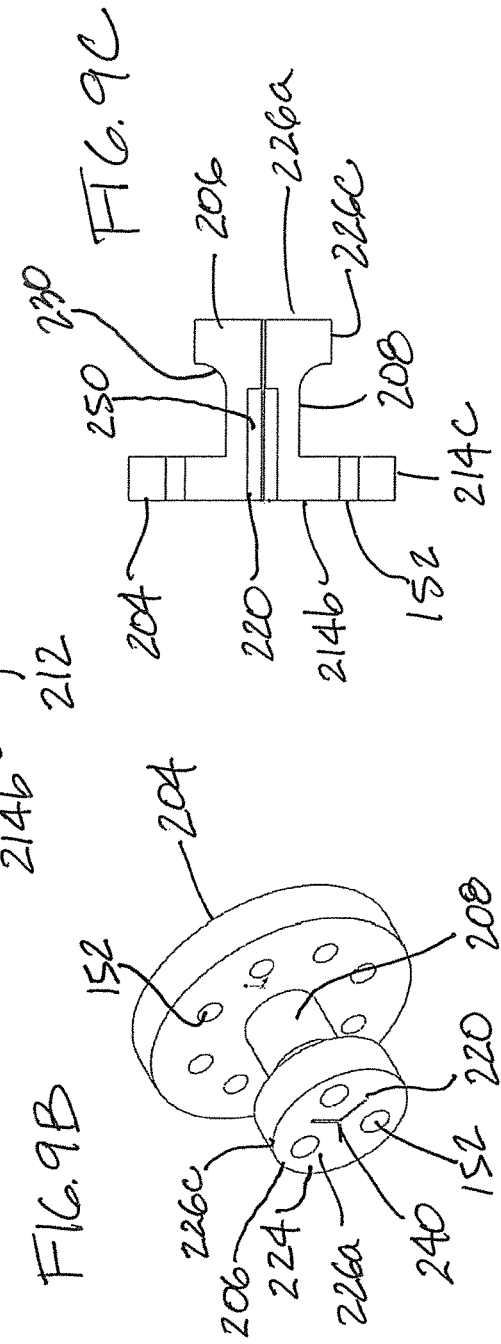

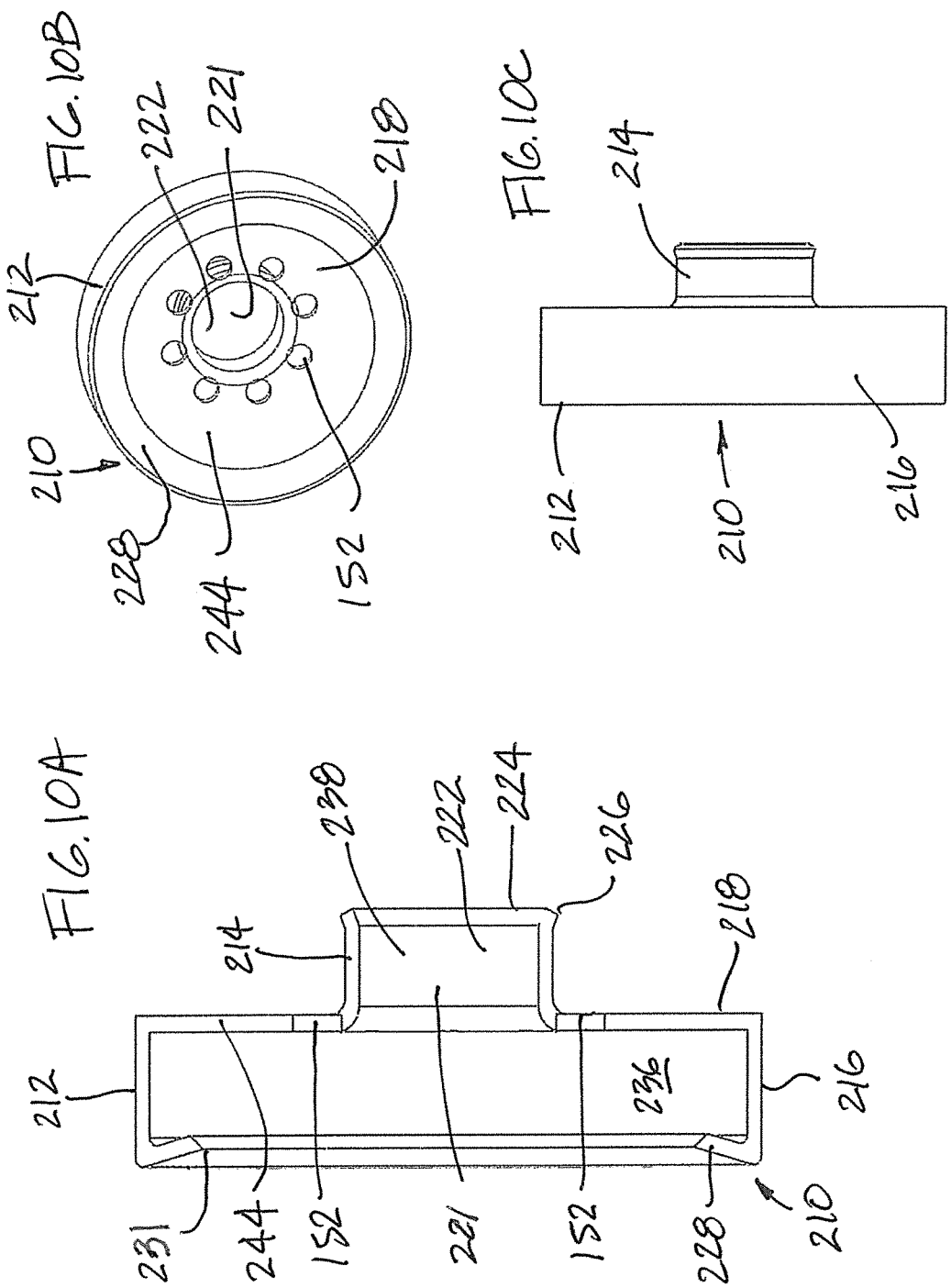

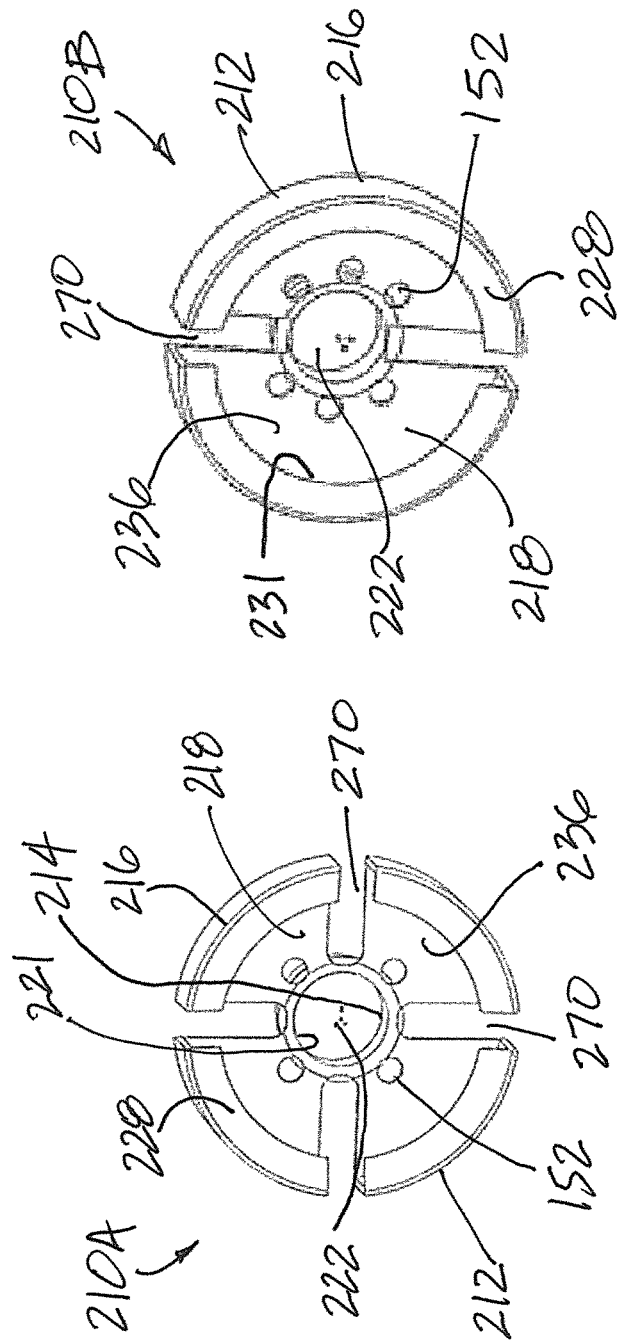

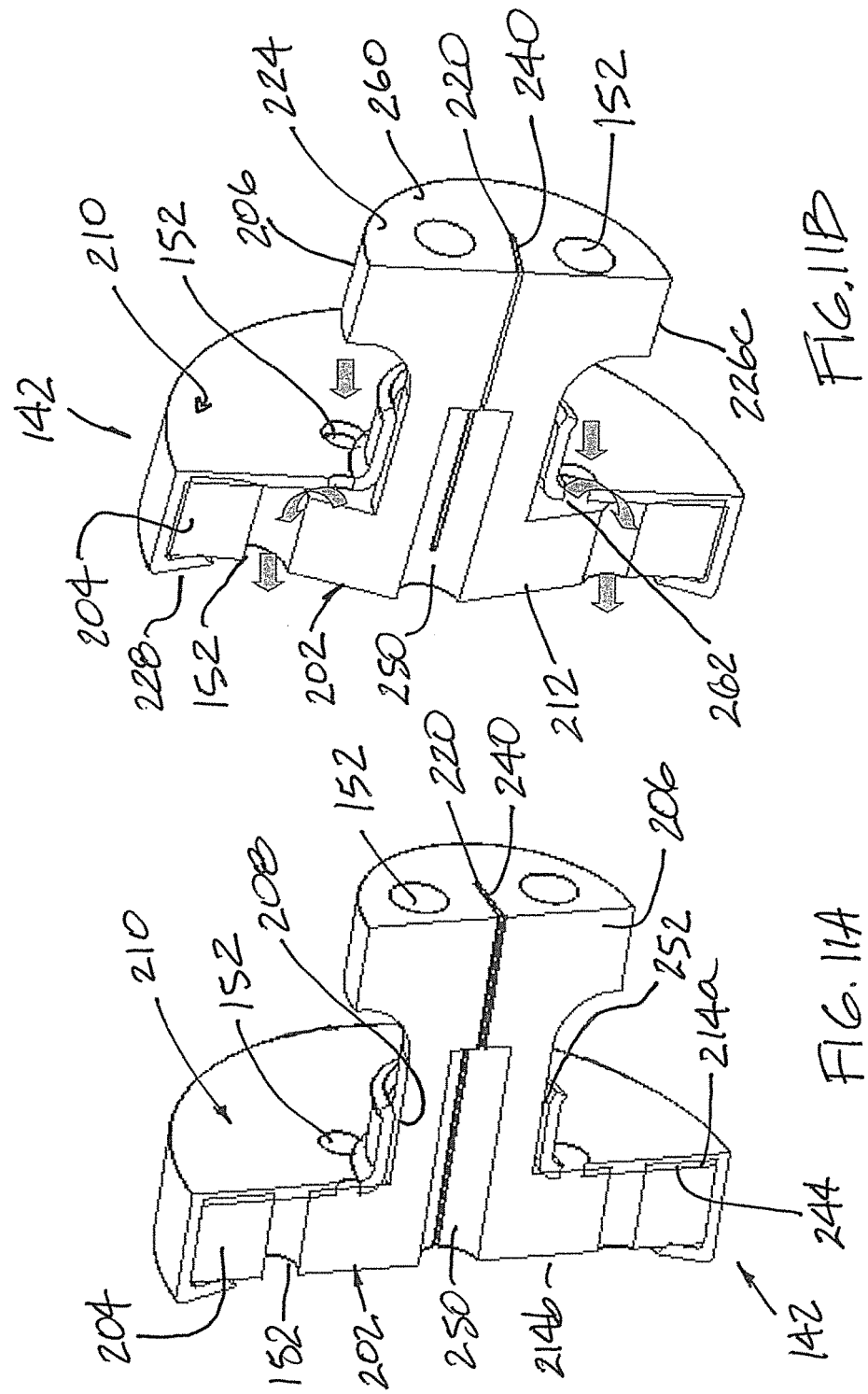

CATHETER DEVICES WITH SEALS AND RELATED METHODS

FIELD OF ART

The disclosed invention generally relates to intravenous (IV) infusion devices, including IV and arterial catheters. In particular, catheter devices and related methods having a flow control system are disclosed.

BACKGROUND

Needle devices are commonly used for a variety of infusion therapies, including infusing fluids into a patient, withdrawing blood from a patient, or monitoring various parameters of the patient's vascular system. A catheter tube connected to a catheter hub is typically connected to an adapter then connects to an IV tubing. Blood control catheters include an internal blood control regulator, such as a valve, that is opened by the insertion of a male Luer or other object into a proximal end of the catheter hub. Thus, following placement of the catheter tube into the vasculature of a patient, an IV fluid source can be connected to the catheter hub, opening the blood control valve. Once connected, fluid from the IV source can begin flow into a patient through the catheter. Conventionally speaking, the proximal end is the end closer to the practitioner and the distal end is further away from the practitioner.

Needle devices often include safety systems that cover the tip of the needle to prevent accidental sticks after placement of the catheter tube into the vasculature of a patient. These systems can be either passive or active. In some systems, the safety features are located inside the catheter hub in the ready position while in other systems they are external of the catheter hub. In either location, the safety features serve the same function, to cover the needle tip in order to prevent accidental needle sticks after venipuncture.

SUMMARY

Aspects of the present disclosure include needle devices. The needle devices described herein can be a catheter assembly. The catheter assembly can be an over the needle catheter or an IV catheter assembly. The catheter assembly can include a catheter tube attached to a catheter hub, a needle attached to a needle hub and projecting through the catheter hub and the catheter tube in a ready position with a needle tip extending distally of a distal opening of the catheter tube. A valve can be placed inside the catheter hub. The valve can be part of a valve system comprising a valve retainer. The valve system can comprise a valve comprising a first valve piece comprising first diameter attached to a second valve piece comprising a second diameter by a valve stem, which has a stem diameter that is smaller than the first diameter and the second diameter, a lumen extending at least partially through the valve stem, and a septum comprising one or more slits located at an end of the lumen, and a valve retainer positioned in the interior cavity of the catheter hub to secure the valve to the interior cavity of the catheter hub.

A further aspect of the present disclosure include a needle device comprising: a catheter tube attached to a catheter hub, said catheter hub comprising a hub body comprising an exterior surface and an interior surface defining an interior cavity; a valve comprising a first valve piece comprising first diameter attached to a second valve piece comprising a second diameter by a valve stem, which has a stem diameter that is smaller than the first diameter and the second diameter, a lumen extending at least partially through the valve stem, and a septum comprising one or more slits located at an end of the lumen; a valve retainer positioned in the interior cavity of the catheter hub to secure the valve to the interior cavity of the catheter hub; and a needle projecting through the valve stem, through the catheter tube, and having a needle tip extending distally of a distal end of the catheter tube in a ready to use position; said needle having a proximal end attached to a needle hub.

Aspects of the present disclosure further include a method for manufacturing a needle device. The method of manufacturing can comprise: attaching a catheter tube attached to a catheter hub, said catheter hub comprising a hub body comprising an exterior surface and an interior surface defining an interior cavity; placing a valve in the interior cavity of the catheter hub, said valve comprising a first valve piece comprising first diameter attached to a second valve piece comprising a second diameter by a valve stem, which has a stem diameter that is smaller than the first diameter and the second diameter, a lumen extending at least partially through the valve stem, and a septum comprising one or more slits located at an end of the lumen; positioning a valve retainer in the interior cavity of the catheter hub to secure the valve to the interior cavity of the catheter hub; and projecting a needle through the valve stem and through the catheter tube so that a needle tip of the needle extends distally of a distal end of the catheter tube in a ready to use position; said needle having a proximal end attached to a needle hub.

An additional aspect of the present disclosure includes a method of using a needle device. The needle device can comprise a catheter hub with a catheter tube, a needle attached to a needle hub, and a valve system located in an interior cavity of the catheter hub. The method of using can comprise: removing the needle and needle hub from the catheter hub and catheter tube; placing a male medical implement into a proximal opening of the needle hub and advancing a section of a valve distally relative to a valve retainer; and said advancing step allows fluid flow to flow around a circumference of a first valve piece or through a plurality of holes of the first valve piece.

The method or apparatus can further include one or more structural features and/or steps described herein.

The needle device can further comprise a valve opener having an end plate for opening the valve.

The needle device wherein the valve opener can have at least one leg attached to the end plate. The valve opener can have two spaced apart legs with each leg attaching to the end plate. The ends of the two legs can be sized and shaped to be pushed by a male medical implement. The end plate can be used to push against the valve or at least part of the valve.

The end plate and the valve retainer can be rotatably fixed relative to one another. In some examples, slots can be used with the valve retainer to allow the legs on the valve opener to rotate relative to the valve retainer.

The needle device wherein the valve retainer can have one or more slots. The one or more slots can cut through an inward rim, a sidewall, and at least part of an end wall of a first cylindrical segment.

The needle device wherein the end plate can include or incorporate a plurality of flow holes.

The needle device can further comprise a centrally positioned hole located centrally of the end plate.

The needle device wherein the valve retainer can comprise two spaced apart slots.

The needle device wherein the end plate and the two legs can be made from plastic or from a metal.

The needle device wherein when two legs are incorporated, each of the two legs can extend through a corresponding one of the two spaced apart slots on the valve retainer.

The needle device wherein the valve retainer can comprise a plurality of flow holes.

The needle device can further comprise a centrally positioned hole located centrally of the valve retainer.

The needle device wherein the second valve piece can occlude the plurality of flow holes of the valve retainer.

The needle device wherein the first valve piece can include a dome top with a planar underside surface.

The needle device wherein the second valve piece can comprise a perimeter that contacts the interior surface of the catheter hub.

The needle device wherein the second valve piece can comprise two spaced apart slots.

The needle device wherein the valve opener can include two legs and wherein each of the two legs can extend through a corresponding one of the two spaced apart slots.

The needle device wherein the first valve piece can be positioned distally of the end plate, the end plate can be positioned distally of the valve retainer, and the valve retainer can be positioned distally of the second valve piece.

The needle device wherein the second valve piece can be deflectable by pushing on the first valve piece in a distal direction.

The needle device wherein the second valve piece can be deflectable by direct contact with a male medical implement.

The needle device can further comprise a gap between a proximally facing wall surface of the end plate and a distally facing wall surface of the valve retainer.

The needle device wherein the first valve piece can comprise a dome top and an opening in communication with the lumen.

The needle device can further comprise a projection located proximally of the valve retainer.

The needle device can further comprise a needle guard comprising a proximal wall, two arms, and two distal walls, and wherein at least part of one of the arms interacts with the projection to retain the needle guard to the catheter hub in the ready to use position.

The needle device wherein fluid flow can be permitted through the valve retainer when the end plate moves distally away from the end plate.

The needle device wherein the end plate can include at least two flow holes that are aligned with two flow holes on the valve retainer. In other examples, one or more than two flow holes can be provided that are aligned with the flow holes on the valve retainer.

The needle device wherein the end plate can include a centrally positioned hole aligned with a centrally positioned hole on the valve retainer.

The needle device wherein the second valve piece has an outer diameter and the first valve piece has an outer diameter, and wherein the outer diameter of the second valve piece can be larger than the outer diameter of the first valve piece.

The needle device wherein the second valve piece has an outer diameter and the first valve piece has an outer diameter, and wherein the outer diameter of the second valve piece can be smaller than the outer diameter of the first valve piece.

The needle device wherein the first valve piece and the second valve piece can omit or can exclude any flow hole.

The needle device wherein the second valve piece can comprise a plurality of flow holes.

The needle device wherein the second valve piece can be located proximally of the first valve piece.

The needle device wherein the valve retainer can include a plurality of flow holes and the first valve piece can include a plurality of flow holes.

The needle device wherein when flow holes are incorporated, the flow holes of the first valve piece and the flow holes of the valve retainer can be out of alignment.

The needle device wherein when flow holes are incorporated, openings of the plurality of flow holes of the first valve piece can be covered by an interior wall surface of the valve retainer.

The needle device wherein the valve retainer can include a holding space and the first valve piece can be located in the holding space.

The needle device can further comprise a rim on the valve retainer pressing against a distally facing wall surface of the first valve piece. The rim on the valve retainer can press the first valve piece against the interior wall surface of the valve retainer.

The needle device wherein the holding space can be located in a first cylindrical segment and wherein a second cylindrical segment can attach to the first cylindrical segment.

The needle device wherein the valve stem can pass through a bore of the second cylindrical segment.

The needle device wherein fluid flow can be permitted when the second valve piece is advanced in the distal direction.

The needle device wherein the second valve piece can have a smaller outer diameter than an outer diameter of the first valve piece.

The needle device wherein fluid flow can be permitted when the first valve piece is at least partially pushed in a distal direction away from the interior wall surface of the valve retainer.

The needle device wherein the first valve piece can be pushed in the distal direction by pushing the second valve piece in the distal direction.

The needle device wherein fluid flow can be permitted when fluid flow passes through a plurality of flow holes in the valve retainer and then through a plurality of flow holes in the first valve piece.

The needle device wherein the needle can comprise a change in profile located proximally of the needle tip.

The needle device can further comprise a needle guard comprising a proximal wall, two arms, and two distal walls located on the needle.

The needle device wherein the needle guard can be located completely inside the interior cavity of the catheter hub.

The needle device wherein the needle guard can be located partially inside the interior cavity of the catheter hub and partially outside of the catheter hub.

BRIEF DESCRIPTION OF THE DRAWINGS

These and other features and advantages of the present devices, systems, and methods will become appreciated as the same becomes better understood with reference to the specification, claims and appended drawings wherein:

FIG. 1 is a cross-sectional side view of a needle device of the present disclosure.

FIG. 1A is a side view of the needle guard of FIG. 1 covering the needle tip of a needle in a in a protective position.

FIG. 2 is a cross-sectional side view of the catheter hub of FIG. 1 with the needle removed and without the catheter tube for clarity.

FIG. 3 is a cross-sectional perspective view of the catheter hub of FIG. 2 shown with a valve retainer and without the valve and the valve opener of FIGS. 1 and 2.

FIGS. 4A and 4B are perspective views of the valve of FIGS. 1 and 2 in the opened and closed positions, respectively.

FIG. 5 is a perspective view of a valve opener of FIGS. 1 and 2.

FIGS. 6A and 6B are partial cross-sectional side views of the catheter hub of FIG. 2 shown in the closed position and opened position, respectively.

FIG. 6C is a partial cross-sectional side view of the catheter hub of FIG. 6B with a male medical implement inserted into the open proximal end to activate the valve.

FIGS. 7A and 7B are cross-sectional perspective view and cross-sectional side view, respectively, of a needle device in accordance with further aspects of the present disclosure, which shows a valve system in a closed position.

FIGS. 8A and 8B are cross-sectional perspective view and cross-sectional side view, respectively, of the needle device of FIGS. 7A and 7B showing the valve system in an opened position.

FIGS. 9A-9C are various views of the valve of FIGS. 7A and 7B.

FIGS. 10A-10C are various views of the valve retainer of FIGS. 7A and 7B.

FIGS. 10D and 10E show alternative valve retainers provided in accordance with aspects of the present disclosure.

FIGS. 11A and 11B are cross-sectional perspective view of the valve system of FIGS. 7A and 7B in the closed position and opened position, respectively.

DETAILED DESCRIPTION

The detailed description set forth below in connection with the appended drawings is intended as a description of the presently preferred embodiments of needle devices provided in accordance with aspects of the present assemblies, systems, and methods and is not intended to represent the only forms in which the present devices, systems, and methods may be constructed or utilized. The description sets forth the features and the steps for constructing and using the embodiments of the present assemblies, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

With reference now to FIG. 1, a cross-sectional side view of a needle device 100, such as an over-the-needle catheter assembly or an IV catheter assembly, provided in accordance with aspects of the present disclosure is shown, which comprises a needle hub 102, a needle 104, a catheter hub 106, and a catheter tube 108. The needle 104 projects distally from a nose section of the needle hub 102 and in through the catheter hub and the catheter tube with the needle tip extending out a distal end of the catheter tube. The needle hub 102 has a flashback chamber and an opening, which can be closed by a vent plug. A valve system 142 comprising a valve 112 and a valve retainer 116 are positioned in the interior cavity 120 of the catheter hub 106. The valve system 142 can further include a valve opener or valve actuator 114. Optionally a needle guard 122 is also provided. As shown, the needle guard 122 is positioned inside the interior cavity 120 of the catheter hub 106, which defines a bore 118. The needle guard 122 is positioned between the two legs 132a, 132b of the valve actuator 114. Said differently, the needle guard 122, when incorporated between the two legs 132a, 132b, has overlapping portions along an axial direction with the valve opener 114 when positioned within the catheter hub 106. For example, the needle guard 122 is not serially positioned with the valve actuator 114 and is positioned between the two legs 132a, 132b such that portions of the needle guard and the valve actuator overlap along an axial direction. The needle guard 122 may be similar to the needle guards disclosed in U.S. Pat. No. 6,616,630, which has two arms 124a, 124b each with a distal wall for blocking the needle tip and a proximal wall comprising perimeter defining a proximal opening having the needle 104 passing therethrough. The needle has a change in profile 128, which can be a crimp, a bulge, a sleeve, or a material buildup, for engaging the perimeter with the proximal opening following placement of the catheter tube 108 into a patient's vein. In some examples, the needle guard is omitted. When incorporated, there needle guard 122 can be positioned completely inside the catheter hub 106, only partially inside the catheter hub 106, or completely outside the catheter hub, such as in a shroud or a separate hub housing between the catheter hub and the needle hub.

FIG. 1A shows a partial side view of the needle 104 and the needle guard 122 of FIG. 1 with the needle tip 110 covered by two distal walls 90a, 90b, such as following successful venipuncture and the needle 104 and needle hub are retracted away from the catheter hub and catheter tube. The two distal walls 90a, 90b can each include a curved lip 92a, 92b or can simply terminate in a straight edge. The change in profile 128 on the needle is shown abutting the proximal wall 126, and more particularly the perimeter defining the opening on the proximal wall. In the example shown, the two arms 124a, 124b intersect one another when view along the side view of FIG. 1A in both the ready position (FIG. 1) and the protective position of FIG. 1A, wherein the needle tip 110 is covered by the needle guard 122. In other examples, the two arms 124a, 124b extend axially from the proximal wall 126 and do not intersect. In still other examples, only a single arm is incorporated. The elbow sections 94a, 94b of the two arms 124a, 124b can engage the projection 136 inside the interior cavity of the catheter hub 106 in the ready position, aided by the needle biasing the two arms outwardly when the needle is located between the two curved lips 92a, 92b in the ready position. During retraction of the needle following successful venipuncture, the needle tip 110 moves proximally of the two distal walls 90a, 90b, which allows the two arms to move radially to cover the needle tip, and the change in profile 128 engages the perimeter defining the opening on the proximal wall 126. Further proximal movement of the needle removes the needle guard 122 from the interior cavity of the catheter hub and the needle tip covered by the needle guard, as shown in FIG. 1A.

FIG. 2 shows the needle device 100 of FIG. 1 after removable of the needle hub 102, the needle 104, and the needle guard 122, such as following successful venipuncture. The catheter hub 106 is shown without the catheter tube 108 for clarity. The catheter hub 106 has a proximal opening 130 that opens into a female Luer, external threads 132, and a tab 131 that may be used as leverage when handling the device 100, such as to push against during insertion or removal of the needle. The valve opener 114 may include two spaced apart legs 132a, 132b connected to an end plate 134. The two space apart legs 132a, 132b have proximal end surfaces 135a, 135b for abutting contact by a male medical implement, such as a syringe type or a male Luer adaptor, when the male medical implement is inserted into the proximal opening 130 to advance the valve opener 114 distally to open the valve 112, as further discussed below. Optionally only one leg is incorporated or more than one legs. Optional connecting piece may be used to fix two or more legs relative to one another, such as to provide support. In some examples, the interior wall surface 140 of the catheter hub can have elongated recesses to accommodate the two legs 132a, 132b so that at least part of each legs are positioned in the elongated recesses. This optional feature can be implemented when the legs 132a, 132b are relatively thick and the recesses formed in the wall surfaces of the catheter hub can accommodate at least some of the thicknesses. The parts of the legs 132a, 132b that are not located in the elongated recesses, such as parts of the two proximal end surfaces 135a, 135b, can be subsequently used to open the valve, such as to be pushed by a male medical implement. As shown in FIG. 1, the two legs 132a, 132b pass along spaces defined between the interior wall surface of the catheter hub and the two sides of the needle guard 122.

A projection 136, which is defined by a first interior diameter located next to a larger second interior diameter, is provided in the interior cavity 120 for retaining the needle guard 122 in the ready to use position shown in FIG. 1 and for retaining the needle guard 122 during retraction of the needle following successful venipuncture. The projection 136 can comprise two or more spaced apart sections and the needle guard 122 can engage the two or more spaced sections of the projection 136 in the ready to use position. The gaps between the spaced sections of the projection 136 allow the two legs 132a, 132b on the valve actuator 114 to extend from a distal position of the projection 136 to a proximal position of the projection, or vice versa. Further, the two legs 132a, 132b of the valve actuator 114 can extend from a distal point through two gaps between the sections of the projection in the proximal direction. As shown, the end plate 134 of the valve opener 114 is positioned distally of the valve retainer 116, which is secured to the interior wall surfaces 140 of the catheter hub 106 to retrain the valve 112 inside the bore 118. The valve retainer 116 can also retain the valve opener 114 inside the catheter hub. The valve 112 shown has a first valve piece 144 connected to a second valve piece 146 by a valve stem 148, which has a hollow interior. In an example, the first valve piece 144 is located distally of the end plate 134, which is located distally of the valve retainer 116, which is located distally of the second valve piece 146. As arranged, movement of the legs in the distal direction causes the end plate to push the first vale piece 144, which is located distally of the second valve piece 126, to pull on the valve stem 148, which causes the second valve piece 146, which is located proximally of first valve piece and the valve stem, to deflect to then permit fluid flow through the valve system 142.

With reference now to FIG. 3, a cut-away perspective view of the catheter hub 106 of FIG. 2 is shown without the valve 112 and valve opener 114 for clarity. The valve retainer 116 is shown wedged inside the bore 118. The valve retainer 116 has a wall 50 with a proximally facing wall surface 52a, a distally facing wall surface 52b, an outside perimeter 150, and a thickness. The valve retainer 116 is wedged distally of the projection 136. As shown, the valve retainer 116 embodies a disc shape. The valve retainer 116 may be made from a bendable material, such as from a thermoplastic material, which allows the disc of the end plate 134 to be distorted to fit distally of the projection 136. In some examples, the projection 136 is omitted and the needle guard 122 is retained in a ready position through different means, such as being held in place by engaging the valve system or employing spring fingers near the proximal wall to engage the interior surface of the catheter hub near the proximal wall. A recess, a shoulder, or other retention surfaces may be provided in the bore 118 of the catheter hub 102 to secure the valve retainer 116 within the interior cavity 120 of the catheter hub 106.

The valve retainer 116 can have a plurality of flow holes 152, such as at least two or more flow holes, and at least one centrally positioned hole 154 to accommodate the valve stem 148 (FIG. 1) in the ready to use position. The centrally positioned hole 154 is preferably larger in diameter than the plurality of flow holes 152. The plurality of holes 152, 154 are configured to permit fluid flow to flow thereacross, as further disused below. In one example, the valve retainer 116 can incorporate eight holes 152 and the centrally positioned hole 154. However, more than eight flow holes or less than eight flow holes are contemplated. The flow holes 152 may be equally spaced around the centrally positioned hole 154. The valve retainer 116 can includes a pair of slots 156a, 156b for accommodating the two legs 132a, 132b (FIG. 1) on the valve actuator 114. This allows for the installation of the end plate 134 of the valve opener 114 distally of the valve retainer 116 while allowing the two legs 132a, 132b to extend through the valve retainer 116 and terminate towards the proximal opening 130 of the catheter hub 106. In practice, the valve system 142 of the present embodiment, which includes the valve 112, valve opener 114, and valve retainer 116, is first assembled in the order shown in FIG. 2 and then placed into the interior cavity 120 together as a unit. In another example, the catheter hub 106 is made from a two-part hub body with a seam therebetween. The valve system 142 may be placed in between the two-part hub body and then the two separate hub pieces secured together with the valve system inside, such as by welding or gluing. The seam for the two-part hub body, when incorporated, can be distal of the Luer taper of the catheter hub. The two part-hub body can be welded, such as by ultrasonic welding, glued together, or combinations thereof. In an example, the seam of the two-part hub body is selected to facilitate assembly of the valve system 142 and/or the valve actuator 114.

With reference now to FIG. 4A, the valve 112 in accordance with aspects of the present disclosure is shown with a septum 160 in the opened position, such as when having the needle projects therethrough as shown in FIG. 1. The first valve piece 144 is shown embodying a dome-shape head, similar to a mushroom head, which has a generally flat or planar underside surface 162 and a rounded or spherical upper side 164, which may also be referred to as a dome top or a mushroom top. In another example, the tip of the first valve piece can be narrow, similar to an arrow. The tip can embody other shapes provided it can fit through the centrally positioned hole 154 of the valve retainer 116 and the end plate 134. The second valve piece 146 can embody a disc comprising a wall surface 166 comprising a proximally facing wall surface 168a, a distally facing wall surface 168b, a circumference 168c, and a thickness. In some examples, the circumference 168c of the second valve piece 146 can be sized and shaped to seal against the interior wall surface 140 of the catheter hub 106 and the second valve piece 146 can be provided with two slots to accommodate the two legs 132a, 132b of the valve opener (FIG. 5). Thus, the diameter of the second valve piece 146 can be wider than the gap between the two legs 132a, 132b with slots provided in the second valve piece 146 to accommodate the two legs. Bumps, projections, recesses, and other surface features may be incorporated on the exterior surface of the circumference 168c to create surface roughness, which can act as flow paths for venting gas. In an example, the surface of the circumference is tapered inwardly as it extends proximally or the circumference can have a generally constant outer diameter.

The valve stem 148 can be connected to the planar underside surface 162 of the first valve piece 144 and the distally facing wall surface 168b of the second valve piece 146. The valve stem 148 can be hollow, as previously described, and can include a septum 160 at one end of the bore and an opening at the other end, such as through the dome top 164. The valve 112 may be made from an elastomeric material, such as from a silicone material, and is preferably elastic. For example, when the valve 112 is stretched by an external force, such as by supporting the distally facing surface 168b and pushing the planar underside surface 162 in the distal direction to pull on the second valve piece 146, the wall surface 166 of the second valve piece 146 can react. As further discussed below, the wall surface 166 can bend or deflect in response to the pulling force by the valve stem 148.

FIG. 4B shows valve 112 with the septum 160 in a closed position, such as when the needle 104 is removed from the valve as shown in FIG. 2. In the closed position, the one or more slits 170 forming one or more flaps on the septum 160 are closed, thus closing the opening leading to the lumen of the valve stem 148 from the second valve piece 146. The second valve piece 146 can be provided with two slots 147a, 147b to accommodate the two legs 132a, 132b of the valve opener (FIG. 5). The slits 170 are shown as a three-point star. In other examples, the slits can have other shapes, such as a single straight slit or an "x-shape" slit.

FIG. 5 shows an exemplary valve opener 114 of the present disclosure. The valve opener 114 may be made from a plastic material and can be unitarily formed with the end plate 134 and the two spaced apart legs 132a, 132b. The end plate 134 has a wall surface 174 comprising a proximally facing wall surface 176a, a distally facing wall surface 176b, a circumference 176c, and a thickness. The end plate 134 can have a disc shape and a plurality of holes, including a plurality of flow holes 152 and a centrally positioned hole 154. In an example, the centrally positioned holes of the end plate 134 and of the valve retainer 116 (FIG. 3) are aligned when positioned inside the catheter hub 106. In another example, the flow holes 152 of the end plate 134 and of the valve retainer 116 (FIG. 3) are aligned when positioned inside the catheter hub 106. In yet other examples, only the centrally positioned holes 154 of the end plate 134 and the valve retainer 116 (FIG. 3) are aligned when positioned inside the catheter hub 106. The flow holes 152 may be equally spaced around the centrally positioned hole 154 of both the end plate 134 and the valve retainer 116. In other examples, the flow holes can be randomly positioned around the centrally positioned hole.

The valve stem 148 of the valve 112 can be sized and shaped to extend through the aligned centrally positioned holes 154 of the end plate 134 and the valve retainer 116. In an example, the dome top or mushroom head 164 of the valve 112, which is pliable and compressible, is first pushed through the centrally positioned hole 154 of the valve retainer 116 and then the centrally positioned hole 154 of the end plate 134 of the valve opener 114. The first valve piece 144 can also be slotted to help with passing through the centrally positioned holes 154 of the end plate and the valve retainer. As shown in FIGS. 1 and 2, the distally facing wall surface 168b of the second valve piece 146 will face the proximally facing wall surface 52a of the valve retainer 116 and the planar underside surface 162 of the dome top 164 will face the distally facing wall surface 176b of the end plate 134 of the valve opener when the valve system is installed inside a catheter hub. The proximally facing wall surface 176a of the end plate faces the distally facing wall surface 52b of the valve retainer 116 when the valve system 142 (FIG. 2) is assembled. Thus, the present valve system 142 can have a first valve piece 144 spaced from a second valve piece 146 with a separately formed and subsequently assembled valve retainer 116 and the end plate 134 located between the two valve pieces 144, 146. In an example, a valve stem 148 can extend through centrally positioned holes 154 of the valve retainer 116 and the end plate 134 and the valve stem 148 is connected at its two ends to the first valve piece 144 and the second valve piece 146. The outside diameter of the valve stem is smaller than the outside diameter of both the first valve piece 144 and the second valve piece 146. In a specific example, the valve stem 148 has a bore or lumen 180 (FIG. 6A) and the second valve piece 146 has a septum 160. In an example, the septum 160 has a plurality of slits, for example one or more slits, that can open to accept a needle passing through the lumen 180 (FIGS. 6A and 6B) of the valve stem 148. The valve opener 114 is not rotatable relative to the valve retainer 116 due to the two legs 132a, 132b extending through the two slots 156a, 156b on the valve retainer 116. However, the two slots 156a, 156b can be enlarged so that at least some relative rotation can occur. The circumference 168c of the second valve piece 146 is configured to be between the two legs 132a, 132b. Said differently, the two legs 132a, 132b have a gap that is sufficiently wide to accommodate the circumference of the second valve piece 146 therebetween.

FIG. 6A shows the needle device 100 of FIG. 1 following removable of the needle 104, the needle hub 102, and the needle guard 122, such as following successful venipuncture. As shown, the valve system 142 is in a closed position. For example, the distally facing wall surface 168b of the second valve piece 146 can rest or abut against the proximally facing wall surface 52a of the valve retainer 116, which can occlude or can block fluid flow through or from the flow holes 152 of the valve retainer 116 and the flow holes 152 of the end plate 134 of the valve opener 114. Thus, fluid flowing in the distal direction, such as from an IV source, is prevented by the wall surface 166 of the valve 112 blocking the flow holes 152. Fluid flowing in the proximal direction, such as blood flow, is also blocked by the wall surface 166 unless fluid pressure is sufficiently high to deflect the wall surface 166 of the valve 112 in the proximal direction. Thus, another aspect of the present disclosure is a provision for controlling the elasticity of the valve 112 and the second valve piece 146, such as by selecting an appropriate thickness, the material type, or the durometer, to either enable or restrict fluid flow in the proximal direction. Material stiffness can also be selected to determine the ease or force needed to open the valve 112 when activated. In the valve closed position of FIG. 6A, the valve retainer 116 and the end plate 134 are spaced from one another a first distance, which can be as little as zero to several millimeters. The two are spaced from one another a second distance, which is larger than the first distance, when the valve system 142 is in an opened position, as further discussed below with reference to FIG. 6B. Also in the valve closed position of FIG. 6A, the planar underside surface 162 of the first end piece 144 and the circumference 168c of the second valve piece 146 are spaced from one another a first distance. The planar underside surface 162 and the circumference 168c are spaced from one another a second distance, which is larger than the first distance, when the valve system 142 is in an opened position, as further discussed below with reference to FIG. 6B.

With reference now to FIG. 6B, the valve system 142 is shown in the opened position to permit fluid flow across the valve 112. A male medical implement can be inserted into the proximal opening 130 of the catheter hub 118 (FIG. 2) to push against the two legs 132a, 132b of the valve opener 114 in the distal direction. This movement causes the end plate 134 of the valve opener 114, in particular the distally facing wall surface 176b of the end plate, to push against the planar underside surface 162 of the first valve piece 144 in the distal direction. This in turn puts the valve stem 148 in tension. As the valve stem 148 is attached to the second valve piece 146 of the valve 112, the tension pulls on the distally facing wall surface 168b of the second valve piece 146 and causes the wall surface 166 of the second valve piece 146 to flex. Consequently, the distally facing wall surface 168b near the circumference 168c of the second valve piece 146 lifts from the valve retainer 116, which opens the flow holes 152 to permit fluid flow in the distal direction, around the circumference 168c of the second valve piece 146 and through the flow holes and out the distal end of the catheter hub and into the catheter tube. As indicated earlier, the second distance between end plate 134 and the valve retainer 116 is increased in the valve opened position. The second distance between the planar underside surface 162 and the circumference 168c is also increased due to the flexing wall surface 166 of the second valve piece 146. When the male medical implement is removed from the proximal opening 130 of the catheter hub 106, the elasticity of the valve 112 recoils to its more relaxed state and returns the valve system 142 to its closed position as shown in FIG. 6A.

FIG. 6C is a schematic cross-sectional side view of the assembly of FIG. 6B shown with a male Luer adaptor 300 positioned in the open proximal end 130 of the catheter hub 106. The male Luer adaptor 300 has a body 306 comprising a Luer tip 302 projecting into the female Luer of the catheter hub 106 and pushing against the proximal end surfaces 135a, 135b of the two legs 132a, 132b to advance the valve actuator 116 in the distal direction. The tip 302 has a distal opening 304 to allow fluid to discharge out through the tip or pulled through the tip. As previously discussed and with reference to FIG. 6B, this movement causes the end plate 134 of the valve opener 114, in particular the distally facing wall surface 176b of the end plate, to push against the planar underside surface 162 of the first valve piece 144 in the distal direction. This in turn puts the valve stem 148 in tension. As the valve stem 148 is attached to the second valve piece 146 of the valve 112, the tension pulls on the distally facing wall surface 168b of the second valve piece 146 and causes the wall surface 166 of the second valve piece 146 to flex. Consequently, the distally facing wall surface 168b near the circumference 168c of the second valve piece 146 lifts from the valve retainer 116, which opens the flow holes 152 to permit fluid flow in the distal direction, around the circumference 168c of the second valve piece 146 and through the flow holes and out the distal end of the catheter hub and into the catheter tube. The male Luer adaptor 300 can represent any number of male medical implements, such as a syringe, a Luer tip of an IV line, etc.

In some examples, the male Luer adaptor 300 has a threaded collar for threaded engagement with the exterior threads 132 on the catheter hub.

FIG. 7A shows another needle device 100 provided in accordance with further aspects of the present disclosure. The needle device 100, which may be a catheter assembly, is shown without several features for clarity, such as without a catheter tube, a needle, and a needle hub. Further, while a needle guard may be incorporated with the present needle device 100, as further discussed below, it is omitted for clarity. The device 100 is shown in a cut-away side perspective view showing a valve system 142 inside an interior cavity 120 of a catheter hub 102, which has a proximal opening 130 for receiving a male medical implement.

A retention shoulder 200, which can be a groove or a projection, is provided with the interior wall surface 140 of the catheter hub 102 for locating the valve system 142 inside the bore 118 of the catheter hub. The retention shoulder 200 can be annular ring with a continuous groove or a projection or can include one or more breaks along the circumference. As shown, the valve system 142 comprises a valve 202 comprising a first valve piece 204 and a second valve piece 206 connected together by a valve stem 208. The first valve piece 204 is shown seated against the shoulder 200 to retain the valve system 142 within the interior cavity 120 of the catheter hub. In an example, the first valve piece 204 can be supported by a valve retainer 210 and the valve retainer can be set against the shoulder 200. In a specific example, the valve retainer 210 has a circumference and the circumference of the valve retainer is held in a groove and the first valve piece 204 is located in the holding space of the valve retainer 210. In some examples, the catheter hub 102 has a female Luer section for receiving a male Luer tip and the retention shoulder 200 can be located distal of the female Luer section to not interfere with the connection with the male Luer tip. In some examples, the catheter hub 102 can be made from a two-part hub with a seam. The retention shoulder 200 can be located at the seam of the two part housing. For example, the two-part housing can be made with a retention shoulder 200 at the seam of the two-part hub to accommodate the circumference of the valve retainer or the valve piece. Once the circumference of the valve retainer or valve piece is placed in the retention shoulder 200, the two-part hub can be joined using welding, adhesive, or combinations thereof.

In an example, the valve stem 208 and/or the second valve piece 206 of the valve system 142 can be located within the female Luer section so that the male Luer tip, when connected to the female Luer section, can contact and advance the second valve piece 206 in the distal direction to open the valve system for fluid flow.

With reference to FIGS. 9A-9C in addition to FIGS. 7A and 7B, the first valve piece 204 has a wall 212, which has a proximally facing wall surface 214a, a distally facing wall surface 214b, a circumference 214c, and a thickness. A plurality of flow holes 152 are incorporated through the thickness of the wall 212 to provide flow paths for fluid flow, as further discussed below. In an example, eight flow holes 152 are provided with more or fewer than eight flow holes contemplated. A centrally positioned hole 154 is provided through the wall 212 and communicate with a lumen of the valve stem 208. One or more reliefs 220 in the form of slits can be provided with the centrally positioned hole 154 to decrease the grip of the bore at the wall 212 with a needle shaft. For example, from a ready to use position in which the needle projects through the valve 202 and the needle tip projects out a distal end of a catheter tube, similar to that shown in FIG. 1, the needle shaft is able to slide more readily when retracted, such as following successful venipuncture, through the lumen of the valve stem 208 and the bore at the wall 212 of the first valve piece 204. The reliefs 220 formed next to or adjacent the centrally positioned hole 154 therefore reduce drag force on the needle when retracting the needle following placement of the catheter tube in a patient.

The second valve piece 206, as more clearly shown in FIG. 9B, has a wall 224, which has a proximally facing wall surface 226a, a distally facing wall surface 226b, a circumference 226c, and thickness. The wall 224 is provided with a plurality of flow holes 152, similar to the wall 212 of the first valve piece 204. In an example, two or more the flow holes 152 can be incorporated with the second valve piece 206. The proximally facing wall surface 226a is configured to be pushed by a male medical implement inserted into the proximal opening 130 of the catheter hub 102 to open the valve 202. Fluid exiting the male medical implement can flow through the flow holes 152 of the second valve piece 206 and/or around the circumference 226 to then flow through the flow holes 152 of the first valve piece, as further discussed below. For example, projections can be provided on the proximally facing wall surface 226a of the second valve piece 206 so that the end surface of the male medical implement does not form a flat or line contact with the proximally facing wall surface. When so provided, some fluid discharged from the male medical implement can flow through the flow holes 152 while some can flow around the circumference 226c.

With reference specifically to FIG. 9C, a ramped section 230 is provided between the second valve piece 206 and the valve stem 208. In an example, a distal end of a needle guard 122 (FIG. 1) can engage the valve 202. For example, the distal end of the needle guard, such as the two distal walls, can grip the valve stem 208 at the ramped section 230. For example, the distal walls of the two arms of the needle guard can extend over the circumference 226c of the second valve piece 206 to grip the valve stem 208 at the ramped section 230. The wall 224 of the second valve piece 206 can also have notches to accommodate the two arms of the needle guard as the arms extend across the wall 224 and the distal walls of the needle guard grip the valve stem 208 at the ramped section 230. With reference again to FIG. 7A, if a needle guard is incorporated, the entire needle guard can be sized and shaped to be positioned inside the bore 118 of the catheter hub 102 while the distal section of the needle guard, such as the two distal walls of the needle guard, grips the valve 202. In another example, part of the needle guard, such as the proximal wall of the needle guard, can be located outside the bore of the catheter hub. In those instances in which the needle guard is partially exposed outside of the catheter hub, the needle hub 102 may be provided with a shroud or other mechanism for engaging the catheter hub in a ready position of the needle device.

With reference again to FIGS. 9B and 9C, the second valve piece 206 has a septum 240, which has one or more slits 220. In the example shown, the septum 240 has a Y-shaped slit resembling a three-point star. In other examples, the septum can have a different slit configuration, such as an X-shaped slit. The one or more slits 220 are formed through the thickness of the second valve piece 206, the wall of the valve stem 208 and the wall of the first valve piece 204. In other examples, the slits can be provided through the thickness of the second valve piece 206 only and not the valve stem 208 or the first valve piece 204. With reference to FIGS. 9A and 9B, the one or more slits 220 are present at both the proximally facing wall surface 226a of the first valve piece and the distally facing wall surface of the first valve piece 204. The lumen 250 is formed through the first valve piece 204 and a majority if not all of the length of the valve stem 208. As shown, the lumen 250 can terminate at about the ramped section 230 of the valve 202. A needle shaft projecting through the septum 240 can experience more resistance at the slits inside the second valve piece 206 and less resistance at the lumen 250 in the valve stem 208 and the first valve piece 204 when it is being retracted away from the valve 202, such as following successful venipuncture. This is due at least in part to the bore 250 being larger than the gap or space at the septum 240.

With reference now to FIGS. 10A, 10B, and 10C, a valve retainer 210 provided in accordance with aspects of the present disclosure is shown in cross-section, end perspective view, and side view, respectively. The valve retainer 210 is sized and shaped to be positioned inside the catheter hub 102 to secure the valve 202 within the bore of the catheter hub. In other examples, the valve 202 can be positioned inside the catheter hub without the valve retainer 210. The valve retainer 210 may be made from a hard material, such as from a hard plastic or from a metal material, such as aluminum or stainless steel. As shown, the valve retainer 210 has a first cylindrical segment 212 and a second cylindrical segment 214, which is attached to and extends from the first cylindrical segment 212 in the proximal direction. The first cylindrical segment 212 is larger than the second cylindrical segment 214, which is understood to mean at least one measurement on the first cylindrical segment 212 that is larger than a corresponding measurement on the second cylindrical segment 214. As shown, the diameter of the first cylindrical segment 212 is larger, the depth is larger, or both the diameter and the depth are larger than the corresponding measurements on the second cylindrical segment 214.

The first cylindrical segment 212 has a sidewall 216 and an end wall 218 having an opening 221 in communication with a bore 222 of the second cylindrical segment 214, which has a proximal opening 224. A perimeter 226 defining the proximal opening 224 can have a flared lip, which can flare radially outwardly of the central axis of the valve retainer 210. When incorporated, this flare section or chamfer can prevent sharp edges and smooth movement of the valve 202 (FIG. 9A) during Luer insertion, as further discussed below. An inwardly extending rim or flange 228 extends from the sidewall 216 of the first cylindrical segment 212 to define a distal opening 231, which has an opening dimension that is smaller than the outside diameter of the sidewall 216. The rim 228 creates a shoulder with the sidewall 216 to retain the first valve piece 204 of the valve 202 of FIG. 9A. Interiorly, the first cylindrical segment 212 has a holding space 236 for accommodating the first valve piece 204 and the second cylindrical segment 214 has a holding space 238 for accommodating the valve stem 208 of the valve 202 (FIGS. 9A, 11A, and 11B).

As best shown in FIG. 10B, a plurality of flow holes 152 are provided with the end wall 218 of the first cylindrical segment 212. In one example, eight flow holes 152 are provided with the end wall 218 with more or fewer flow holes contemplated. The flow holes 152 can be evenly spaced from one another around the opening 221 on the end wall 218. In other examples, the flow holes 152 are not evenly spaced from one another around the opening 221. When the valve 202 of FIG. 9A is coupled to the valve retainer 210 of FIG. 10A, as further discussed below, the flow holes 152 of the valve retainer 210 do not align with the flow holes 152 on the first valve piece 204. For example, after installation, the openings of the plurality of flow holes 152 on the proximally facing wall surface 214a of the first valve piece 204 contact or abut the interior wall surface 244 (FIG. 10B) of the first cylindrical section 212 and are not aligned with the flow holes 152 of the wall 244. The openings of the flow holes 152 of the valve retainer 210 also contact the proximally facing wall surface 214 of the second valve piece 206 of the valve 202. The contact between the two are further urged by the rim 228 of the first cylindrical segment 212 pressing against the distally facing wall surface 214b of the first valve piece 204 to urge the proximally facing wall surface 214a of the first valve piece 204 against the interior wall surface 244 of the first cylindrical section 212. Thus, when the valve 202 is mounted inside the valve retainer 210, the flow holes 152 of both the first valve piece and the interior wall surface are occluded and fluid cannot flow thereacross, such as cannot flow from the proximal direction to the distal direction or from the distal direction to the proximal direction due to the openings of the flow holes 152 being in contact with the interior wall surface 244 of the end wall 218 and the flow holes of the end wall in contact with wall surfaces of the first valve piece. The valve 202 being placed inside the valve retainer 210 and in a closed position is more clearly shown in FIGS. 7B, 11A and 11B. As shown, fluid flow (represented by the arrows) attempting to flow through the flow holes 152 of the valve retainer 210 and the flow holes 152 of the valve 202 are blocked by the surface contacts and the off-alignment configuration of the two sets of flow holes 152.

Fluid flow can be completely blocked or a small amount of flow, such as a small seepage, can pass through when the openings of the flow holes 152 contact the interior wall surface 24 of the valve retainer 210. However, fluid flow is permitted when the openings of the flow holes 152 are pushed away from the interior wall surface 244 of the end wall 218, such as by pushing the second valve piece 206 in the distal direction with a male medical implement to flex the first valve piece away from the interior wall surface 244, as further discussed below.

FIG. 10C is a side view of the valve retainer 210 of FIG. 10A. In some examples, the exterior surface of the sidewall 216 can be provided with bumps, channels, or recesses to create an un-even outer surface. This un-even outer surface allows for gas venting to flow between the interior wall surface of the catheter hub and the sidewall 216 of the valve retainer.

FIG. 10D is a partial front perspective view of a valve retainer 210A provided in accordance with aspects of the present disclosure. The present valve retainer 210A is similar to the valve retainer of FIGS. 10A-10C with a few exceptions. In the present embodiment, the valve retainer 210A incorporates a plurality of slots or slits 270. Each slot 270 can cut through a plurality of surfaces of the first cylindrical segment 212. As shown, each slot 270 can cut through the inward rim 228, the sidewall 216, and the end wall 218. In an example, each slot 270 can cut completely through the length or width dimension of the inward rim 228 and the sidewall 216. The slot 270 can also cut through a substantial dimension, such as a substantial part of the diameter, of the end wall 218, up to about the opening 221 of the end wall leading to the bore 222. However, each slot 270 can cut only through part of the end wall 218, well short of the opening to the bore 222. In an example, four slots 270 are incorporated. However, the number of slots 270 can be greater than four slots or fewer than four slots. When incorporated, the slots 270 can allow the structure of the first cylindrical segment 212 to flex to allow the first valve piece 204 of the valve 202 of FIGS. 9A-9C to be pressed fit into the holding space 236 of the first cylindrical segment 212. The slots 270 also allow the assembled valve system 142 to easily flex during installation into the interior cavity of a catheter hub. This allows the valve system 142 with the present slotted valve retainer to be used with a single hub body configuration. Alternatively, the valve system 142 with the present slotted valve retainer may be used with a two-part catheter hub body.

When the slots 270 are incorporated, fewer flow holes 152 can be formed in the end wall 218 than when no slots 270 are included. As shown, four flow holes 152 are provided in the end wall 218. However, fewer than four flow holes 152 or greater than four flow holes 152 can be included. The slots 270 and the flow holes 152 on the first cylindrical segment 212 should not align with any of the flow holes 152 of the first valve piece 204 when the valve system is in a closed position, as further discussed below.

In some examples, one or more lengthwise slots, running lengthwise with the bore 222, can be incorporated on the second cylindrical segment 214. The slots on the second cylindrical segment 214 can be included to facilitate assembly of the valve 202 into the valve retainer 210A.

FIG. 10E is a partial front perspective view of a valve retainer 210B provided in accordance with aspects of the present disclosure. The present valve retainer 210B is similar to the valve retainer 210 of FIGS. 10A-10C and the valve retainer 210A of FIG. 10D. In the present embodiment, only two slots 270 are incorporated. With only two slots 270, more flow holes 152 can be incorporated in the end wall 218 than the end wall 218 of the embodiment of FIG. 10D.

With reference now to FIG. 11A, the valve system 142 is shown in perspective view and in a closed position in which at least part of the proximally facing wall surface 214a of the first valve piece 204 of the valve 202 contacts the interior wall surface 244 of the valve retainer 210. The valve system 142 is in the closed position and is similar to the configuration shown in FIGS. 7A and 7B. As shown, the flow holes 152 of the valve retainer 210 and the flow holes 152 of the valve 202 are not aligned, as previously described. Thus, fluid cannot flow or is restricted across the two sets of flow holes 152 when the valve system 142 is in the closed position shown. Also shown is a closed slit 220, which is the position of the septum 240 when the needle shaft is removed from the septum 240 and from the bore 250 of the valve 202 following successful venipuncture.

The flow holes 152 of the second valve piece 206 on the valve 202 are spaced from the valve retainer 210 and spaced from the first valve piece 204. In an example, the flow holes 152 of the valve retainer 210 are spaced from the flow holes 152 of the second valve piece 206 by a gap. The gap can be the length of the valve stem 208 or increments thereof. The flow holes 152 of the first valve piece 204 are also spaced from the flow holes of the second valve piece 206 by a gap. The gap can be the length of the valve stem 208 or increments thereof. The bore 222 (FIG. 10A) of the second cylindrical segment 214 of the valve retainer 210 may be sized and shaped so as to provide a clearance gap 252 with the exterior of the valve stem 208. This allows the valve stem 208 to move more readily when compressed by a male medical implement. Further, the clearance gap 252 provides room for the valve stem 208 to expand and/or deflect when the second valve piece 206 is pressed distally by the male medical implement should the valve stem undergo compression or bending. In some examples, the valve stem 208 simply transfers the force in the distal direction to the first valve piece without expanding and/or deflecting. The second valve piece 206 may be sufficiently pliable so as to be squeezed through the bore 222 of the second cylindrical segment 214 during installation of the valve 202 to the valve retainer 210. The second valve piece 206 may incorporate slots or gaps to facilitate the installation. In some examples, a hard thermoplastic, such as an elongated rod, may be added to the second valve piece 206, such as by co-molding, insert-molding, or during post-molding, to add rigidity so that the second valve piece can be pressed by a male Luer tip to activate the valve.

With reference now to FIG. 11B, the valve system 142 of FIG. 11A is shown in an activated or opened position. The valve system 142 in the opened position is also shown in FIGS. 8A and 8B, which show the valve system 142 inside a catheter hub 102 in a side cross-sectional perspective view and a side cross-sectional view, respectively. To activate the valve system 142, which is held axially fixed inside the catheter hub 102 against a shoulder 200, a male medical implement, such as a male Luer adaptor or a syringe tip, is inserted into the proximal opening 130 of the catheter hub 102 (FIGS. 8A and 8B) to push against the proximally facing wall surface 226a of the second valve piece 206. The second valve piece 206 has a wall 224 that is sized and shaped to be pushed by an end surface of a tip of a male medical implement. For example, the outer surface 260 near the circumference 226c is sized and shaped to be abutted by a tip of a male medical implement to advance the second valve piece 206 in the distal direction. When a sufficient distally directed force is applied to the second valve piece 206, the force can cause the valve stem 208 to advance in the distal direction and transfer the force to the first valve piece 204. As the wall 212 of the first valve piece 204 is elastic, it can flex under the applied force and bows axially in the distal direction. Because the first valve piece 204 is held around its outer perimeter by the rim 228 of the valve retainer 210, the wall flexes more readily at or near the centrally positioned hole 154 in the distal direction.

As best shown in FIG. 11B, flexing of the wall 212 results in separation between the proximally facing wall surface 214a of the valve 202 and the interior wall surface 244 of the valve retainer 210 to create a gap or spacing 262. With the gap or spacing 262 between the proximally facing wall surface 214a of the valve 202 and the interior wall surface 244 of the valve retainer 210, the valve system 142 can be said to be in an opened position. The flexing of the first valve piece 204 can be caused at least in part by a distally directed force on the second valve piece 206. Thus, if fluid is now discharged out the tip of the male medical implement, the fluid can first flow through the flow holes 152 of the second valve piece 206, then through the flow holes 152 of the valve retainer 210, then through the gap 262 and through the flow holes 152 of the first valve piece 204, and then eventually through the catheter tube and into the patient. Once the valve system 142 is in the opened opposition, a sample from the patient can also be drawn through the valve 202 by generating a vacuum at the male medical implement, such as by retracting on a plunger of a syringe to create a vacuum within the syringe barrel. Fluid can flow in the reverse order just described when drawing a sample.

To close the valve system 142, the male medical implement is first retracted in the proximal direction away from the proximal opening 130 of the catheter hub 102. As the valve 202 is elastic and its outer perimeter held by the rim 228 of the valve retainer 210, the wall 212 returns to its less flexed state or its normal state when not loaded by any external force. In an example, the valve 202 moves from the flexed position shown in FIG. 11B to its less flexed state shown in FIG. 11A to move the valve system 142 from an opened state or position to a closed state or position.

The valve system 142 of FIGS. 11A and 11B may be practiced with the valve retainer 210A of FIG. 10D or the valve retainer 210B of FIG. 10E.

Methods of making and of using the needle devices shown and described elsewhere herein are within the scope of the present disclosure.

Although limited embodiments of the needle devices and their components have been specifically described and illustrated herein, many modifications and variations will be apparent to those skilled in the art. Furthermore, it is understood and contemplated that features specifically discussed for one needle device embodiment may be adopted for inclusion with another needle device embodiment, provided the functions are compatible. For example, release element may be integrated with the needle guard. Accordingly, it is to be understood that the needle devices and their components constructed according to principles of the disclosed device, system, and method may be embodied other than as specifically described herein. The disclosure is also defined in the following claims.

What is claimed is:

1. A needle device comprising:
    a catheter tube attached to a catheter hub, said catheter hub comprising a hub body comprising an exterior surface and an interior surface defining an interior cavity;
    a valve comprising a first valve piece, a second valve piece, a valve stem, a lumen, and a septum, the first valve piece comprising a first diameter and the second valve piece comprising a second diameter, the first valve piece being attached to the second valve piece by the valve stem, the valve stem having a stem diameter that is smaller than the first diameter and the second diameter, the lumen extending at least partially through the valve stem, and the septum comprising one or more slits located at an end of the lumen;
    a valve retainer positioned in the interior cavity of the catheter hub to secure the valve to the interior cavity of the catheter hub, the valve retainer is in contact with the interior surface of the hub body and comprises a surface; and
    a needle projecting through the valve stem, through the valve retainer, through the catheter tube, and having a needle tip extending distally of a distal end of the catheter tube in a ready to use position; said needle having a proximal end attached to a needle hub.

2. The needle device of claim 1, further comprising a valve opener having an end plate for opening the valve.

3. The needle device of claim 2, wherein the valve opener has at least one leg attached to the end plate.

4. The needle device of claim 2, wherein the end plate is located between the first valve piece and the second valve piece.

5. The needle device of claim 1, wherein the valve retainer comprises two spaced apart slots.

6. The needle device of claim 5, further comprising a valve opener comprising an end plate and two legs.

7. The needle device of claim 1, wherein the first valve piece has a dome top with a planar underside surface.

8. The needle device of claim 1, wherein the second valve piece comprises a perimeter that contacts the interior surface of the catheter hub.

9. The needle device of claim 8, wherein the second valve piece comprises two spaced apart slots.

10. The needle device of claim 1, wherein the second valve piece is deflectable by pushing on the first valve piece in a distal direction.

11. The needle device of claim 1, wherein the first valve piece comprises a dome top and an opening in communication with the lumen.

12. The needle device of claim 1, further comprising a projection located proximally of the valve retainer.

13. The needle device of claim 1, wherein the second valve piece has an outer diameter and the first valve piece has an outer diameter, and wherein the outer diameter of the second valve piece is larger than the outer diameter of the first valve piece.

14. The needle device of claim 1, wherein the second valve piece has an outer diameter and the first valve piece has an outer diameter, and wherein the outer diameter of the second valve piece is smaller than the outer diameter of the first valve piece.

15. The needle device of claim 1, wherein the second valve piece comprises a plurality of flow holes.

16. The needle device of claim 1, wherein the second valve piece is located proximally of the first valve piece.

17. The needle device of claim 1, wherein the valve retainer has a plurality of flow holes and the first valve piece has a plurality of flow holes.

18. The needle device of claim 1, wherein the valve retainer has a holding space and the first valve piece is located in the holding space.

19. The needle device of claim 1, wherein fluid flow is permitted when the second valve piece is advanced in a distal direction.

20. The needle device of claim 1, wherein the needle comprises a change in profile located proximally of the needle tip.

21. The needle device of claim 1, further comprising a needle guard comprising a wall for blocking the needle tip located to a side of the needle in the ready to use position and the wall movable distally of the needle tip in a protected position.

22. The needle device of claim 21, wherein the needle comprises a change in profile located proximally of the needle tip for engaging the needle guard in the needle guarded position.

23. The needle device of claim 1, wherein the valve stem has a generally constant outside diameter and a bore.

24. The needle device of claim 23, wherein the second valve piece comprises two spaced apart slots.

25. A needle device comprising:
a catheter tube attached to a catheter hub, said catheter hub comprising a hub body comprising an exterior surface and an interior surface defining an interior cavity;
a valve comprising a first valve piece, a second valve piece, a valve stem, a lumen, and a septum, the first valve piece comprising a first diameter and the second valve piece comprising a second diameter, the first valve piece being attached to the second valve piece by the valve stem, the valve stem having a stem diameter that is smaller than the first diameter and the second diameter, the lumen extending at least partially through the valve stem, and the septum comprising one or more slits located at an end of the lumen;
a valve retainer positioned in the interior cavity of the catheter hub to secure the valve to the interior cavity of the catheter hub; and
a needle projecting through the valve stem, through the catheter tube, and having a needle tip extending distally of a distal end of the catheter tube in a ready to use position; said needle having a proximal end attached to a needle hub,
wherein the valve retainer comprises a plurality of flow holes.

26. The needle device of claim 25, further comprising a centrally positioned hole located centrally of the valve retainer.

27. The needle device of claim 25, further comprising a valve opener having an end plate for opening the valve.

28. The needle device of claim 27, wherein the valve opener has at least one leg attached to the end plate and extends in a proximal direction.

29. The needle device of claim 25, wherein the valve retainer comprises two spaced apart slots.

30. The needle device of claim 25, further comprising a valve opener comprising an end plate and two legs, said end plate located between said first valve piece and said second valve piece.

31. The needle device of claim 25, further comprising a needle guard comprising a wall for blocking the needle tip located to a side of the needle in the ready to use position, and the wall movable distally of the needle tip in a protected position.

32. The needle device of claim 31, wherein the needle comprises a change in profile located proximally of the needle tip for engaging the needle guard in the needle guarded position.

33. The needle device of claim 25, wherein the second valve piece is deflectable by pushing on the first valve piece in a distal direction, the first valve piece being located distally of the second valve piece.

34. The needle device of claim 25, wherein the second valve piece has an outer diameter and the first valve piece has an outer diameter, and wherein the outer diameter of the second valve piece is larger than the outer diameter of the first valve piece.

35. The needle device of claim 25, wherein the second valve piece has an outer diameter and the first valve piece has an outer diameter, and wherein the outer diameter of the second valve piece is smaller than the outer diameter of the first valve piece.

36. The needle device of claim 25, wherein the second valve piece comprises a plurality of flow holes.

37. The needle device of claim 25, wherein the valve retainer has a holding space and the first valve piece is located in the holding space.

38. The needle device of claim 25, wherein fluid flow is permitted when the second valve piece is advanced in a distal direction.

39. A method for manufacturing a needle device comprising:
attaching a catheter tube attached to a catheter hub, said catheter hub comprising a hub body comprising an exterior surface and an interior surface defining an interior cavity;
placing a valve in the interior cavity of the catheter hub, said valve comprising a first valve piece, a second valve piece, a valve stem, a lumen, and a septum, the first valve piece comprising a first diameter and the second valve piece comprising a second diameter, the first valve piece being attached to the second valve by the valve stem, the valve stem having a stem diameter that is smaller than the first diameter and the second diameter, the lumen extending at least partially through the valve stem, and the septum comprising one or more slits located at an end of the lumen;

positioning a valve retainer comprising a plurality of flow holes in the interior cavity of the catheter hub to secure the valve to the interior cavity of the catheter hub, the valve retainer is in contact with the interior surface of the hub body and comprises a surface; and projecting a needle through the valve stem, the valve retainer, and through the catheter tube so that a needle tip of the needle extends distally of a distal end of the catheter tube in a ready to use position; said needle having a proximal end attached to a needle hub.

40. The method of claim 39, further comprising projecting the needle through a needle guard, said needle guard comprising a wall for blocking the needle tip located to a side of the needle in the ready to use position, and the wall movable distally of the needle tip in a protected position.

41. The method of claim 40, wherein the needle comprises a change in profile located proximally of the needle tip for engaging the needle guard in the needle guarded position.

* * * * *